US012778505B2

(12) United States Patent
Tan et al.

(10) Patent No.: US 12,778,505 B2
(45) Date of Patent: Nov. 3, 2026

(54) ELECTRONIC DEVICE AND BIOELECTRICAL SIGNAL ACQUISITION METHOD

(71) Applicant: Honor Device Co., Ltd., Shenzhen (CN)

(72) Inventors: Yinjiong Tan, Shenzhen (CN); Liang Bai, Shenzhen (CN); Ruiying Shang, Shenzhen (CN); Yi Liu, Shenzhen (CN)

(73) Assignee: Honor Device Co., Ltd., Shenzhen (CN)

( * ) Notice: Subject to any disclaimer, the term of this patent is extended or adjusted under 35 U.S.C. 154(b) by 769 days.

(21) Appl. No.: 18/016,066

(22) PCT Filed: Aug. 19, 2022

(86) PCT No.: PCT/CN2022/113752
§ 371 (c)(1),
(2) Date: Jan. 13, 2023

(87) PCT Pub. No.: WO2023/098154
PCT Pub. Date: Jun. 8, 2023

(65) Prior Publication Data

US 2024/0245355 A1 Jul. 25, 2024

(30) Foreign Application Priority Data

Nov. 30, 2021 (CN) ......................... 202111444025.7

(51) Int. Cl.
*A61B 5/00* (2006.01)
*A61B 5/0537* (2021.01)
(Continued)

(52) U.S. Cl.
CPC ............ *A61B 5/681* (2013.01); *A61B 5/0537* (2013.01); *A61B 5/256* (2021.01); *A61B 5/282* (2021.01);
(Continued)

(58) Field of Classification Search
CPC ....... A61B 5/681; A61B 5/256; A61B 5/6824; A61B 5/6831
See application file for complete search history.

(56) References Cited

U.S. PATENT DOCUMENTS 4,375,219 A * 3/1983 Schmid .................. A61B 5/332
600/396
11,116,448 B1 * 9/2021 Trapero Martin ... A61B 5/0816
(Continued)

FOREIGN PATENT DOCUMENTS

CN 108251819 A 7/2018
CN 110794666 A 2/2020
(Continued)

*Primary Examiner* — Joseph A Stoklosa
*Assistant Examiner* — William Mossbrook
(74) *Attorney, Agent, or Firm* — Leydig, Voit & Mayer, Ltd.

(57) ABSTRACT

An electronic device and a bioelectrical signal acquisition method are provided. The electronic device includes a rear housing, a plurality of first contact electrodes, and a plurality of second contact electrodes. A first contact area and a second contact area are distributed on the rear housing. The plurality of first contact electrodes/second contact electrodes are spaced on the rear housing respectively and electrically connected to each other. The first contact electrode and the second contact electrode are used for contacting with the skin respectively to form a bioelectrical signal acquisition circuit. At least one first contact electrode and at least one second contact electrode are distributed in the first contact area, and at least one first contact electrode and at least one second contact electrode are distributed in the second contact area.

19 Claims, 11 Drawing Sheets

(51) Int. Cl.

*A61B 5/256* (2021.01)
*A61B 5/282* (2021.01)
*G04G 17/08* (2006.01)

(52) U.S. Cl.

CPC ........ *G04G 17/08* (2013.01); *A61B 2562/046* (2013.01)

(56) References Cited

U.S. PATENT DOCUMENTS

| | | | | |
|---|---|---|---|---|
| 11,156,965 | B1 | 10/2021 | Trapero | |
| 2018/0042557 | A1 | 2/2018 | Park et al. | |
| 2019/0239769 | A1 | 8/2019 | Lee et al. | |
| 2021/0275102 | A1 | 9/2021 | Cho et al. | |
| 2021/0290120 | A1 | 9/2021 | Al-Ali et al. | |
| 2022/0151554 | A1* | 5/2022 | Jang | A61B 5/339 |
| 2022/0256720 | A1 | 8/2022 | Takagi | |
| 2022/0257131 | A1 | 8/2022 | Rayer | |
| 2023/0124396 | A1* | 4/2023 | Gong | A61B 5/02233 368/10 |
| 2024/0206791 | A1* | 6/2024 | Wang | A61B 5/02427 |

FOREIGN PATENT DOCUMENTS

| | | | | |
|---|---|---|---|---|
| CN | 210843062 | U | 6/2020 | |
| CN | 111358463 | A | 7/2020 | |
| CN | 111712191 | A | 9/2020 | |
| CN | 111973174 | A | 11/2020 | |
| CN | 211962040 | U | 11/2020 | |
| CN | 112535482 | A | 3/2021 | |
| CN | 214252912 | U | 9/2021 | |
| CN | 113633291 | A * | 11/2021 | A61B 5/369 |
| CN | 216569972 | U | 5/2022 | |
| CN | 114911151 | A | 8/2022 | |
| WO | 2021004995 | A1 | 1/2021 | |
| WO | 2021020687 | A1 | 2/2021 | |

* cited by examiner

ELECTRONIC DEVICE AND BIOELECTRICAL SIGNAL ACQUISITION METHOD

CROSS-REFERENCE TO RELATED APPLICATIONS

This application is a national stage of International Application No. PCT/CN2022/113752, filed on Aug. 19, 2022, which claims priority to Chinese Patent Application No. 202111444025.7, filed on Nov. 30, 2021. The disclosures of both of the aforementioned applications are hereby incorporated by reference in their entireties.

TECHNICAL FIELD

This application relates to the field of wearable devices, and specifically, to an electronic device and a bioelectrical signal acquisition method.

BACKGROUND

Wearable devices such as electronic watches and bracelets may be used for measuring bioelectrical signals such as an electrocardiogram signal and a body composition electrical signal of a wearer.

However, the wearable devices in conventional technologies have poor contact reliability with skin of the wearer, which affects the acquisition of the bioelectrical signal by the devices.

SUMMARY

This application provides an electronic device and a bioelectrical signal acquisition method to resolve the problem that the acquisition of the bioelectrical signal is affected by the poor contact reliability of the wearable devices with the skin of the wearer in conventional technologies.

According to a first aspect, an embodiment of this application provides an electronic device, including: a housing, a plurality of first contact electrodes, and a plurality of second contact electrodes. The housing includes a rear housing, where a first contact area and a second contact area are distributed on the rear housing; The plurality of first contact electrodes are spaced on the rear housing and electrically connected to each other on an inner side of the rear housing, and the first contact electrode is at least partially exposed to an outer side of the rear housing. The plurality of second contact electrodes are spaced on the rear housing and electrically connected to each other on the inner side of the rear housing; and the second contact electrode is at least partially exposed to the outer side of the rear housing. The second contact electrode and the first contact electrode are distributed on the rear housing and insulated from each other. At least one first contact electrode and at least one second contact electrode are distributed in the first contact area, and at least one first contact electrode and at least one second contact electrode are distributed in the second contact area.

When a user wears the electronic device in this embodiment of this application, if the wear is normal or tight, the first contact area and the second contact area are both in contact with the skin of the wearer. In this case, because there are the plurality of first contact electrodes and the plurality of second contact electrodes, it is easy to ensure that the first contact electrode and the second contact electrode are in contact with the skin. If the wear is loose, the housing may tilt to one side due to gravity or other causes, so that one of the first contact area and the second contact area leaves the skin of the wearer. In this case, because the first contact electrode and the second contact electrode are both distributed in the first contact area, and the first contact electrode and the second contact electrode are also both distributed in the second contact area, even if the housing tilts to one side, it can still be ensured that the first contact electrode and the second contact electrode are in contact with the skin.

In a possible implementation, the first contact area and the second contact area are spaced on the rear housing along a first direction, and the rear housing has a middle area between the first contact area and the second contact area.

In this implementation, the middle area may be used for separating the first contact area and the second contact area, so that other structures of the electronic device, such as a charging pogo pin (Pogo Pin) or other measuring electrodes/sensors, may be arranged between the two.

In a possible implementation, the electronic device further includes a charging pogo pin, and the charging pogo pin is arranged in the middle area.

In this implementation, the charging pogo pin of the electronic device is arranged in the middle area, which can realize a charging function of the electronic device.

In a possible implementation, the rear housing has a convex annular area, and a plurality of contact electrodes spaced from each other are distributed in the annular area along a circumferential direction. One side of the annular area is the first contact area, and there is at least one first contact electrode and one second contact electrode among the contact electrodes distributed in the first contact area. Another side of the annular area is the second contact area, and there is at least one first contact electrode and one second contact electrode among the contact electrodes distributed in the second contact area.

In this implementation, the convex annular area arranged on the rear housing is used for distributing and arranging the contact electrode, which is conducive to the contact between the contact electrode and the skin of the wearer.

In a possible implementation, a quantity of the contact electrodes is 2N, and N is a positive integer, where N contact electrodes are the first contact electrodes, and the other N contact electrodes are the second contact electrodes. The N first contact electrodes are sequentially adjacent in the annular area along the circumferential direction, and the N second contact electrodes are sequentially adjacent in the annular area along the circumferential direction; or, the N first contact electrodes and the N second contact electrodes are arranged alternately along the circumferential direction.

In this implementation, for the case where the first contact electrodes/second contact electrodes are sequentially adjacent, the first contact electrodes/second contact electrodes are distributed intensively, and the electrical connection wiring between the first contact electrodes/second contact electrodes is simple and convenient. For the case where the first contact electrodes and the second contact electrodes are sequentially arranged alternately, it is easier to ensure that the at least one first contact electrode and the one second contact electrode are in contact with the skin of the wearer.

In a possible implementation, the contact electrode is arc-shaped.

In this implementation, the contact electrode is arc-shaped, so that the contact electrodes can form a circular circumferential distribution form, which achieves beautiful appearance, and is conducive to the contact between the contact electrode and the skin of the wearer.

In a possible implementation, the rear housing includes a main housing plate and a circular plate protruding outwards from a central position of the main housing plate. The first contact area and the second contact area are both located on the circular plate.

This implementation is favorable for the first contact area and the second contact area to contact with the skin of the wearer.

In a possible implementation, a plurality of accommodating slots spaced along the circumferential direction are provided on an outer side surface of the circular plate, and the accommodating slots are used for accommodating the first contact electrodes or the second contact electrodes. The first contact electrode and the second contact electrode are respectively exposed to the outer side surface of the circular plate.

This implementation is conducive to the determining of the positions of the first contact electrode and the second contact electrode, and during wear, the first contact electrode and the second contact electrode can be pressed between the skin of the wearer and a bottom surface of the accommodating slot, which is favorable for the first contact electrode and the second contact electrode to contact with the skin of the wearer.

In a possible implementation, through holes penetrating from bottom surfaces of the accommodating slots to an inner side surface of the circular plate are further provided on the circular plate. A first conductive plate and a second conductive plate are arranged on the inner side of the rear housing. The first contact electrodes are electrically connected to the first conductive plate through a conductive member penetrating the corresponding through holes, and the second contact electrodes are electrically connected to the second conductive plate through a conductive member penetrating the corresponding through holes.

In this implementation, the conductive connection of the first contact electrodes and the conductive connection of the second contact electrodes are respectively implemented through the first conductive plate and the second conductive plate arranged on the inner side of the rear housing.

In a possible implementation, the accommodating slot is arc-shaped.

In this implementation, the accommodating slot is arc-shaped and suitable for matching with the arc-shaped contact electrode.

In a possible implementation, the electronic device further includes a charging pogo pin. A via is further provided on the circular plate, and the via is used for allowing the charging pogo pin to be exposed to the outer side surface of the circular plate. The via is located on the circumference where the accommodating slots are located and at a position of the circular plate between the adjacent accommodating slots.

In this implementation, the charging pogo pin and the contact electrodes are both arranged on the circular plate, so that the space arrangement is proper. While the problems of complex structural coordination and poor sealing caused by the charging pogo pin penetrating the contact electrode are avoided, the proper distribution of the first contact electrode and the second contact electrode is ensured, so as to facilitate the formation of a bioelectrical signal acquisition circuit.

In a possible implementation, the housing includes a main frame, the main frame has a front opening and a rear opening, and the rear housing is connected to the rear opening of the main frame.

In this implementation, a rear cover of the housing is used as a rear closed structure of the main frame.

In a possible implementation, the first contact electrode and/or the second contact electrode are made of conductive materials.

In this implementation, the first contact electrode/the second contact electrode may adopt electrode materials such as stainless steel.

In a possible implementation, the first contact electrode and/or the second contact electrode include a substrate and a conductive layer on a surface of the substrate.

In this implementation, the first contact electrode/the second contact electrode may further contact and conduct electricity with the skin by arranging the conductive layer on a surface of a non-conductive substrate.

In a possible implementation, the housing further includes a printed circuit board. The first contact electrode and/or the second contact electrode are electrically connected to the printed circuit board through a conductive member. Optionally, the conductive member is conductive foam or a conductive metal dome.

In this implementation, the first contact electrode and/or the second contact electrode receive a bioelectrical signal from the skin of the wearer and can transmit the bioelectrical signal to the printed circuit board through the conductive member for processing and analysis. The conductive foam or the conductive metal dome has a certain elasticity, and can adapt to the jumping of the spacing between the first contact electrode/the second contact electrode and the printed circuit board within a certain range, which is conducive to the reliability of electrical connection.

In a possible implementation, the printed circuit board includes an analog front-end (AFE) chip, and the AFE chip is electrically connected to the first contact electrode and the second contact electrode respectively to acquire and/or process electrical signals from the first contact electrode and the second contact electrode.

In this implementation, the AFE chip can pre-sample the signals transmitted by the first contact electrode and the second contact electrode.

In a possible implementation, the electronic device is an electronic watch or an electronic bracelet.

In this implementation, the electronic device is an electronic watch or an electronic bracelet, which may be worn on a wrist of the wearer to contact with the skin on the wrist of the wearer and acquire the relevant bioelectrical signal of the wearer from the wrist.

Certainly, in other implementations, the wearable device may also be a device worn in other positions, such as a ring worn on a finger.

In a possible implementation, the electronic device is an electronic watch and the housing is a dial of the electronic watch. The electronic watch further includes a chain connected to the housing. The housing has a first connecting ear and a second connecting ear oppositely arranged along a second direction, and two ends of the chain are respectively connected to the first connecting ear and the second connecting ear to form a circle with the housing for being worn on a human wrist. The first contact area and the second contact area are spaced on the rear housing along a first direction, and the rear housing has a middle area between the first contact area and the second contact area. The electronic watch further includes two charging pogo pins, and the two charging pogo pins are spaced in the middle area along the second direction. When the electronic watch is worn on the human wrist, the first direction is a long direction along the human wrist, and the second direction is a long direction perpendicular to the human wrist.

The electronic device in this implementation is an electronic watch, and a natural state of hands of the wearer is that the hands hang down. In this case, the first direction is along a gravity direction. That is, the first contact area and the second contact area are distributed up and down. When the wear is tight, it can be ensured that the first contact area and the second contact area are both in contact with the wrist to ensure the acquisition of the bioelectrical signal. When the wear is loose, the dial of the electronic watch is restrained by gravity and the chain. Although the upper one of the first contact area and the second contact area tilts and leaves the wrist skin, the lower one of the first contact area and the second contact area is pressed against the wrist skin. That is, one of the first contact area and the second contact area is in contact with the wrist skin. In addition, either of the first contact area and the second contact area is arranged with the first contact electrode and the second contact electrode, so that the bioelectrical signal can also be acquired.

In a possible implementation, the first contact electrode and the second contact electrode are ECG electrodes or body composition detection electrodes.

This implementation may be used for the acquisition of an electrocardiogram signal or a body composition signal.

According to a second aspect, an embodiment of this application provides a bioelectrical signal acquisition method. A detected object wears the foregoing electronic device, and at least one of the first contact area or the second contact area is made to contact with skin of the detected object, so that at least one first contact electrode and at least one second contact electrode are in contact with the skin of the detected object to form a bioelectrical signal acquisition circuit, thereby acquiring a bioelectrical signal of the detected object.

The bioelectrical signal acquisition method in this embodiment of this application adopts the foregoing electronic device, which can adapt to the requirements of acquiring the bioelectrical signal when the wear is loose or tight, and ensure the reliability of signal acquisition.

In a possible implementation, the bioelectrical signal is an electrocardiogram signal or a body composition electrical signal.

The bioelectrical signal acquisition method of this implementation may be used for the acquisition of the electrocardiogram signal or the body composition signal.

BRIEF DESCRIPTION OF DRAWINGS

To describe the technical solutions of the embodiments of this application more clearly, the following briefly describes the accompanying drawings of the embodiments. It should be understood that, the following accompanying drawings show only some embodiments of this application, which cannot be considered as limitation on the scope. A person of ordinary skill in the art may still derive other accompanying drawings from the accompanying drawings without creative efforts.

DESCRIPTION OF MAIN COMPONENT SYMBOLS

Figure 1:
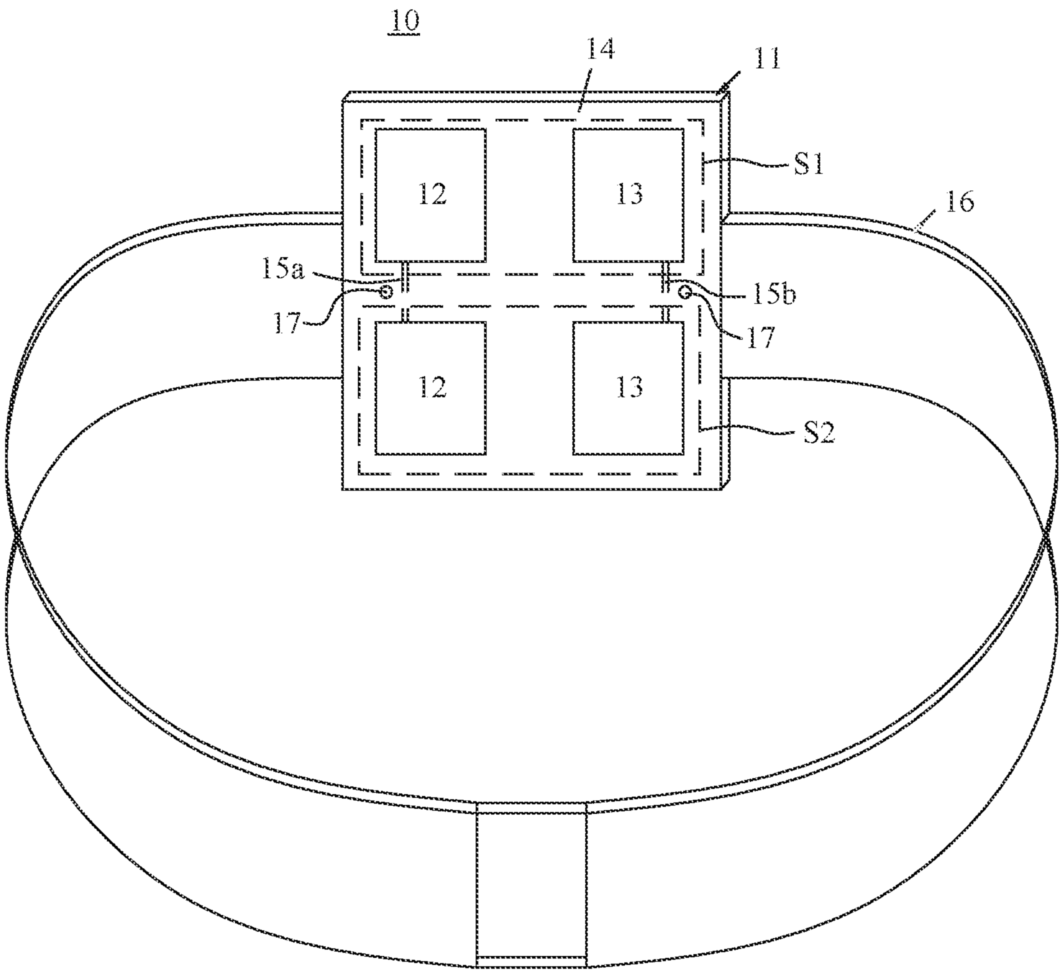
FIG. 1 is a schematic structural diagram of an electronic device according to an embodiment of this application.

| | |
|---|---|
| Electronic device | 10 |
| Electronic watch | 10a |
| Housing | 11 |
| First contact electrode | 12 |
| Second contact electrode | 13 |
| Rear housing | 14 |
| Flexible printed circuit | 15a |
| Flexible printed circuit | 15b |
| Ring belt | 16 |
| Charging pogo pin | 17 |
| Dial | 18 |
| Chain | 19 |
| Display screen | 20 |
| Main frame | 21 |
| Bioelectrical signal acquisition circuit | 22 |
| Main housing plate | 23 |
| Circular plate | 24 |
| Printed circuit board | 25 |
| Conductive member | 26 |
| AFE chip | 27 |
| First conductive plate | 28 |
| Second conductive plate | 29 |
| Substrate | 30 |
| Conductive layer | 31 |
| First connecting ear | 32 |
| Second connecting ear | 33 |
| Wearer | 80 |
| Wrist | 81 |
| Skin | 82 |
| First contact point | D1 |
| Second contact point | D2 |
| Conductive circuit | D3 |
| Internal space | Q1 |
| Accommodating slot | Q2 |
| Through hole | Q3 |
| Via | Q4 |
| Groove | Q5 |
| First contact area | S1 |
| Second contact area | S2 |
| Partition area | S3 |
| Annular area | S4 |
| First direction | Y1 |
| Second direction | Y2 |

DESCRIPTION OF EMBODIMENTS

The technical solutions in the embodiments of this application are clearly and completely described in the following with reference to the accompanying drawings in the embodiments of this application. Apparently, the described embodiments are merely some rather than all of the embodiments of this application.

It should be noted that when a component is referred to as "being fixed to" another component, the component may be directly on the another component, or an intervening component may be present. When a component is considered to be "connected to" another component, the component may be directly connected to the another component, or an intervening component may also be present. When a component is considered to be "arranged" on another component, the component may be directly arranged on the another component or an intervening component may also be present. The terms "vertical", "horizontal", "left", and "right" and similar expressions used in this specification are merely used for the purpose of description.

Unless otherwise defined, meanings of all technical and scientific terms used in this specification are the same as that usually understood by a person skilled in the art to which this application belongs. In this application, terms used in the specification of this application are merely intended to describe objectives of the specific implementations, but are not intended to limit this application. The term "or/and" used in this specification includes any or all combinations of one or more related listed items.

Some implementations of this application are described below in detail. The implementations and features in the implementations may be combined with each other in the case of no conflict.

Embodiment

An embodiment of this application provides an electronic device, which may be an electronic device worn on a wrist such as an electronic watch or bracelet, or a head-mounted electronic device such as smart glasses and goggles, or an electronic device worn on feet, torso or other positions, configured to acquire a bioelectrical signal, such as an electrocardiogram signal, during wear.

The electronic device in this embodiment of this application may be applied to human body or other animals.

Referring to FIG. 1, an electronic device 10 in this embodiment of this application includes a housing 11, a plurality of first contact electrodes 12, and a plurality of second contact electrodes 13.

For example, when the electronic device 10 is an electronic device configured to acquire an electrocardiogram signal, the corresponding first contact electrode 12/second contact electrode 13 is an ECG electrode. The acquired electrocardiogram signal may be processed to generate an electrocardiograph (ECG), which is used for recording the electrical activity of the heart and assisting in diagnosing heart diseases. When the electronic device 10 is configured to acquire a body composition electrical signal (such as human body resistance) or another bioelectrical signal, the corresponding first contact electrode 12/second contact electrode 13 is another electrode structure.

In this implementation, the first contact electrode and the second contact electrode may be made of the same conductive material or different conductive materials. For example, the composition materials of the first contact electrode 12 and the second contact electrode 13 are both metal materials such as stainless steel and, copper, or other non-metallic conductive materials.

Still referring to FIG. 1, the housing 11 includes a rear housing 14, where the rear housing 14 refers to a housing facing and is used for contacting one side of skin of a wearer during wear. A first contact area S1 and a second contact area S2 are distributed on the rear housing 14. The plurality of first contact electrodes 12 are spaced on the rear housing 14 and electrically connected to each other on an inner side (referring to one side of the rear housing away from the skin of the wearer, the same below) of the rear housing 14, for example, electrically connected to each other through a flexible printed circuit (FPC) 15*a* arranged on the inner side of the rear housing 14. The first contact electrode 12 is at least partially exposed to an outer side of the rear housing 14. Similarly, the plurality of second contact electrodes 13 are spaced on the rear housing 14 and electrically connected to each other on the inner side of the rear housing 14, for example, electrically connected to each other through a flexible printed circuit 15*b* arranged on the inner side of the rear housing 14. The second contact electrode 13 is at least partially exposed to the outer side of the rear housing 14. The first contact electrode 12 and the second contact electrode 13 are distributed on the rear housing 14 and insulated from each other. For example, the rear housing 14 is made of non-conductive materials such as ceramics, and the first contact electrode 12 and the second contact electrode 13 are spaced on the rear housing 14, so that the first contact electrode 12 and the second contact electrode 13 are distributed on the rear housing 14 and insulated from each other. The first contact electrode 12 and the second contact electrode 13 are used for contacting with the skin of the wearer respectively, and are connected to a printed circuit board (PCB) (not shown in FIG. 1) in the electronic device 10 to form a bioelectrical signal acquisition circuit. To be exposed to the rear housing 14 to contact with the skin and to be electrically connected on the inner side of the rear housing 14 at the same time, a hole may be provided on the rear housing 14. The first contact electrode 12/the second contact electrode 13 is arranged at the corresponding hole, and the outer sides thereof are exposed to the rear housing 14, and the inner side thereof are directly electrically connected to each other or electrically connected to each other through other conductive structures. At least one first contact electrode 12 and at least one second contact electrode 13 are distributed in the first contact area S1, and at least one first contact electrode 12 and at least one second contact electrode 13 are distributed in the second contact area S2.

Figure 2:
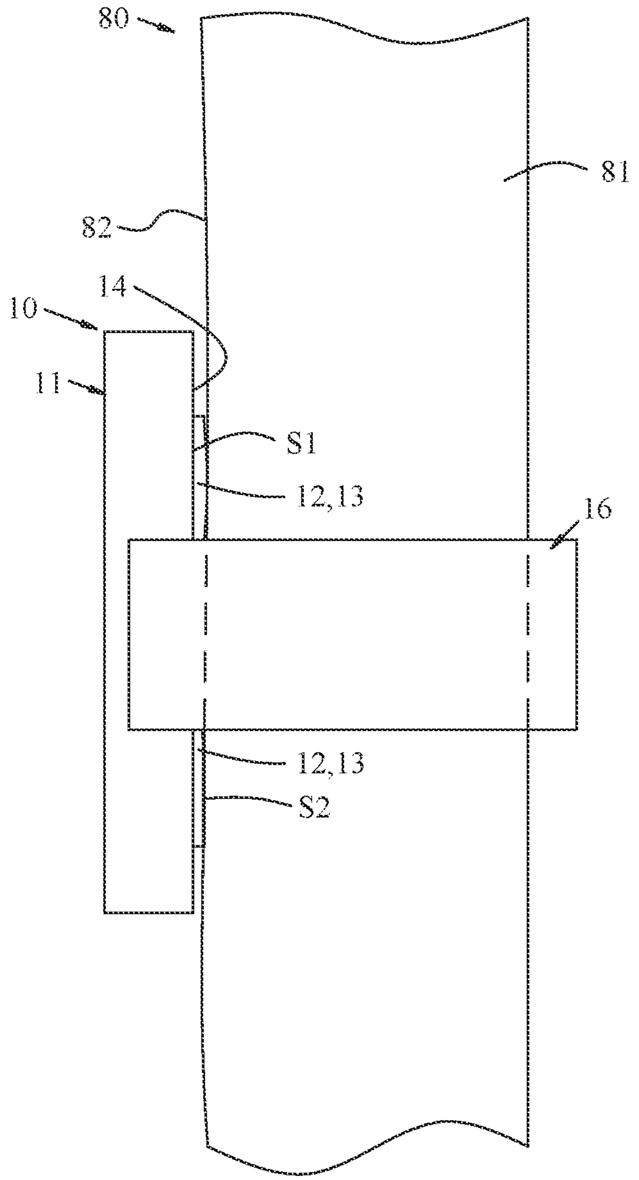
FIG. 2 is a schematic diagram of a wear state of the electronic device in FIG. 1.

Referring to FIG. 1 and FIG. 2, the electronic device 10 is arranged with a ring belt 16. The ring belt 16 is connected to the housing 11, and used for being worn on a wrist 81 or other parts of a wearer 80, and make the rear housing 14 fit to skin 82 of the wearer 80.

FIG. 2 is a schematic diagram of a wear state of the electronic device 10 in FIG. 1. The first contact area S1 and the second contact area S2 are distributed up and down. In FIG. 2, the wear of the electronic device 10 is tight or normal, the first contact area S1 and the second contact area S2 are both in contact with the skin 82 of the wearer 80.

Figure 3:
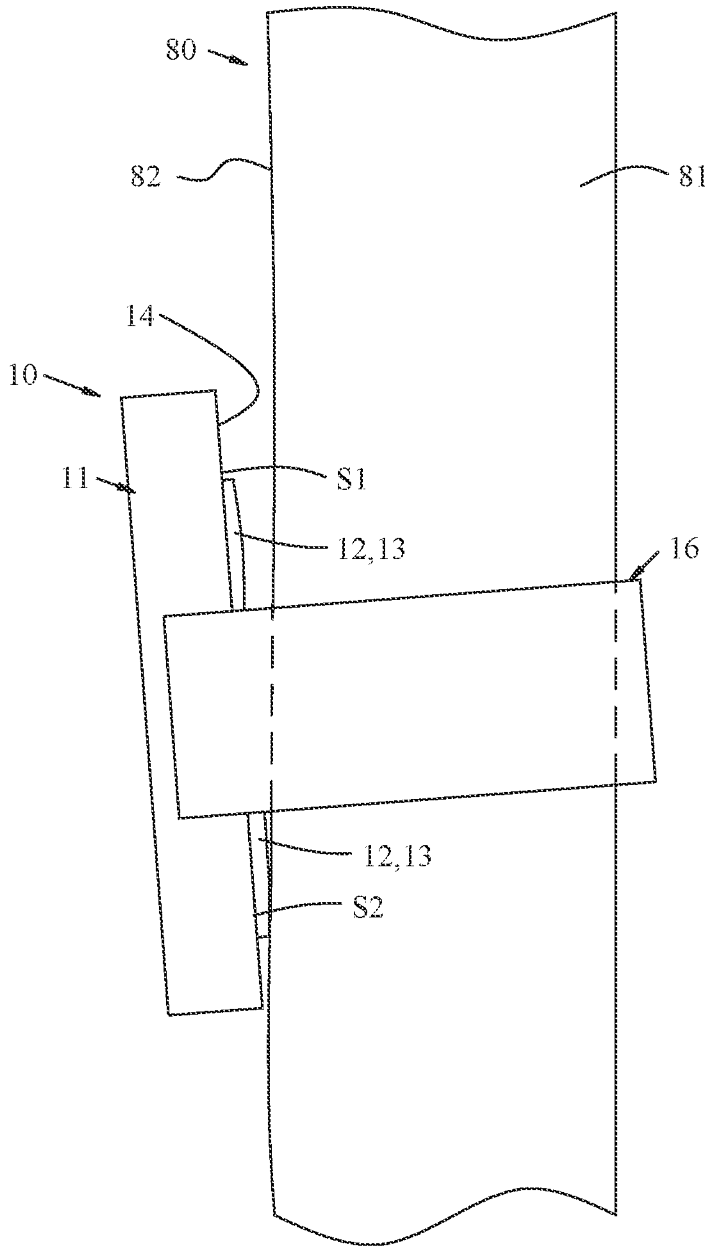
FIG. 3 is a schematic diagram of another wear state of the electronic device in FIG. 1.

When a user wears the electronic device 10 in this embodiment of this application, if the user wear is normal or tight (as shown in FIG. 2), the first contact area S1 and the second contact area S2 are both in contact with the skin 82 of the wearer 80. In this case, because there are the plurality of first contact electrodes 12 and the plurality of second contact electrodes 13, it is easy to ensure that the first contact electrode 12 and the second contact electrode 13 are in contact with the skin 82. If the wear is loose (as shown in FIG. 3), the housing 11 and an internal mounting structure may tilt to one side due to gravity or other causes, so that at least one of the first contact area S1 and the second contact area S2 cannot fully contact with the skin 82. In this case, because the first contact electrode 12 and the second contact electrode 13 are both distributed in the first contact area S1, and the first contact electrode 12 and the second contact electrode 13 are also both distributed in the second contact area S2, even if the housing 11 tilts to one side, it can still be ensured that the first contact electrode 12 and the second contact electrode 13 are in contact with the skin 82. As shown in FIG. 3, the upper one (the first contact area S1) of the first contact area S1 and the second contact area S2 tilts and leaves the skin 82 of the wearer 80, and the lower one (the second contact area S2) of the first contact area S1 and the second contact area S2 is pressed against the skin 82 of the wearer 80. The first contact electrode 12 and the second contact electrode 13 distributed thereon are respectively in contact with the skin 82 to form a bioelectrical signal acquisition circuit.

In this embodiment, all or part of a housing surface of the rear housing 14 may be used as the contact area to contact with the skin 82 of the wearer. The first contact area S1 and the second contact area S2 are both part of the contact area of the rear housing 14. For example, the first contact area S1 may be part of the contact area of the rear housing 14 far away from the skin 82 in the wear state shown in FIG. 3, and the second contact area S2 is part of the contact area of the rear housing 14 near the skin 82 in the wear state shown in FIG. 3.

Therefore, the electronic device 10 in this embodiment of this application has good contact reliability with the skin 82 of the wearer 80, and can better adapt to different wear states A position of the rear housing 14 between the first contact electrodes 12 and/or a position between the second contact electrode 13 may be used for arranging a charging pogo pin 17 (Pogo Pin), so that the electronic device 10 can adapt to a charging base for paired use (not shown in the figure). In this way, the electronic device 10 can further be compatible with a previous generation charging base (not shown in the figure) with charging contact points arranged at corresponding positions.

Some implementations of this embodiment are described below.

Figure 4:
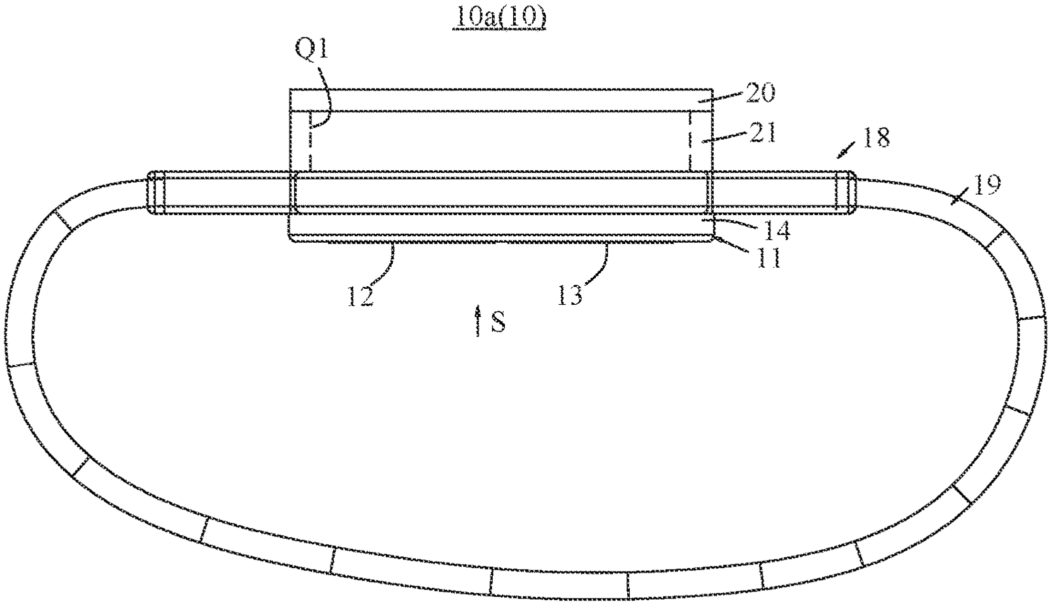
FIG. 4 is a schematic structural diagram of an electronic device according to another embodiment of this application.
Figure 5:
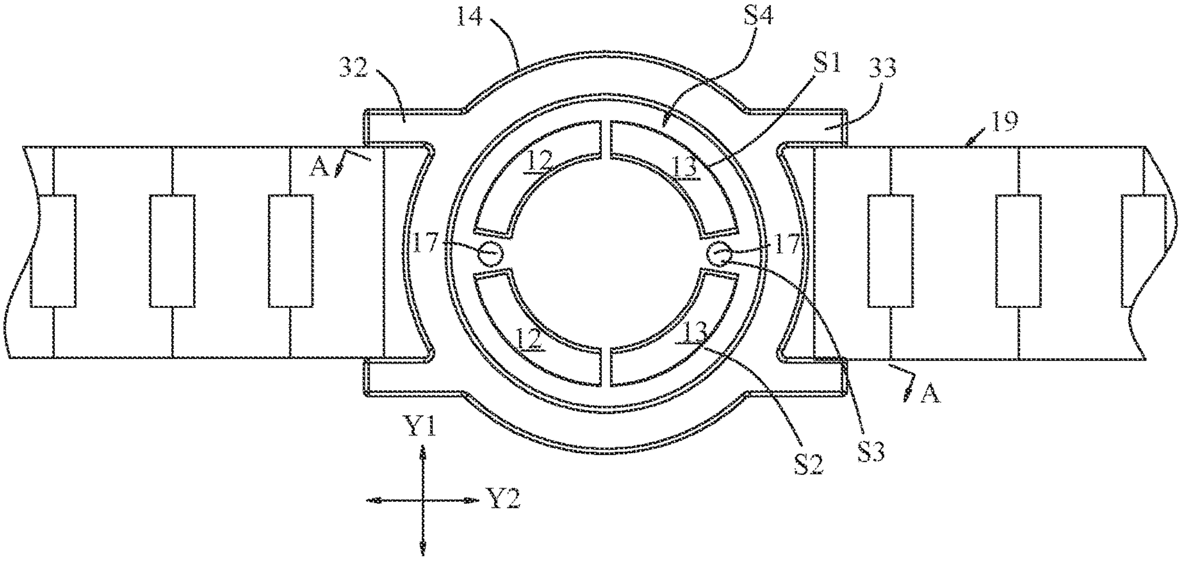
FIG. 5 is an S-direction view of an electronic device in FIG. 4 (chain is only shown in part)

Referring to FIG. 4 to FIG. 5, the electronic device 10 in this implementation is an electronic watch 10*a*, configured to be worn on a human body, to acquire a human electrocardiogram signal.

Referring to FIG. 4 and FIG. 5, the electronic device 10 in this implementation includes the housing 11 (that is, an outer housing of a dial 18 of the electronic watch 10*a*), the plurality of first contact electrodes 12, and the plurality of second contact electrodes 13. The housing 11 is connected to a chain 19 for being worn on the wrist of the wearer.

Referring mainly to FIG. 4, the dial 18 of the electronic watch 10*a* includes the housing 11 and other structures installed inside the housing 11 (such as an electronic component or other functional components, which are not shown in FIG. 4). The housing 11 is mainly used for determining an outer contour of the dial 18 and to define an internal space Q1 for installing other structures. In the electronic device 10 with a display function such as the electronic watch 10*a*, the dial 18 is closed by the incompletely closed housing 11 and a display screen 20.

As shown in FIG. 4, the housing 11 of the dial 18 includes a main frame 21 and the rear housing 14. The main frame 21 has a front opening and a rear opening. The rear housing 14 is connected to the rear opening of the main frame 21, and the display screen 20 is connected to the front opening of the main frame 21 to form the basically closed internal space Q1, which is used for installing various functional components (such as a battery or a printed circuit board) or structural members (such as a positioning support structure used for supporting or positioning and installing various functional components) of the device body.

In other implementations, the composition of the dial 18 may further be arranged as needed, for example, the rear housing 14 and the main frame 21 are arranged as a whole. The display screen 20 may also be replaced by a front housing, thereby obtaining the dial 18 without the display screen.

Figure 6:
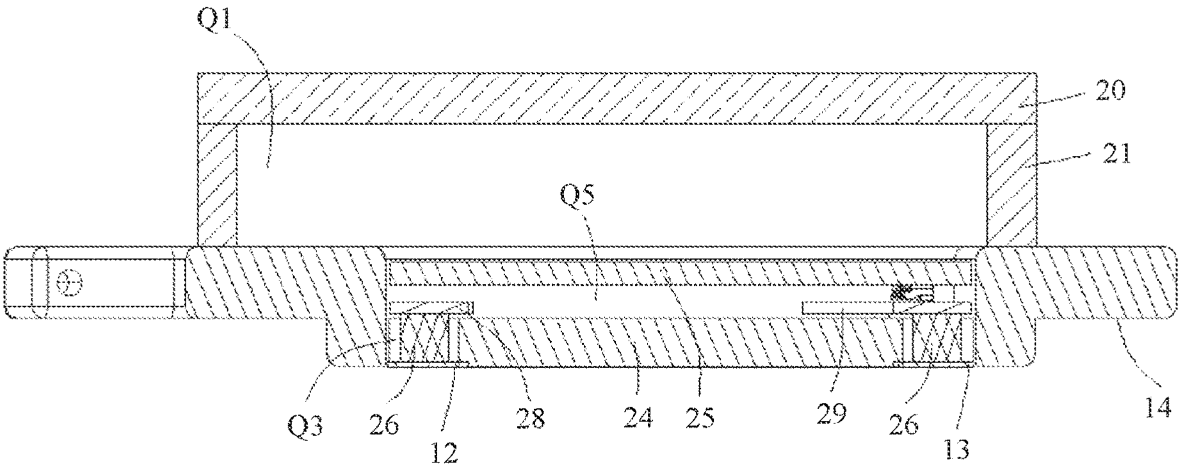
FIG. 6 is a sectional view of a dial part of the electronic device in FIG. 5 along line A-A.
Figure 7:
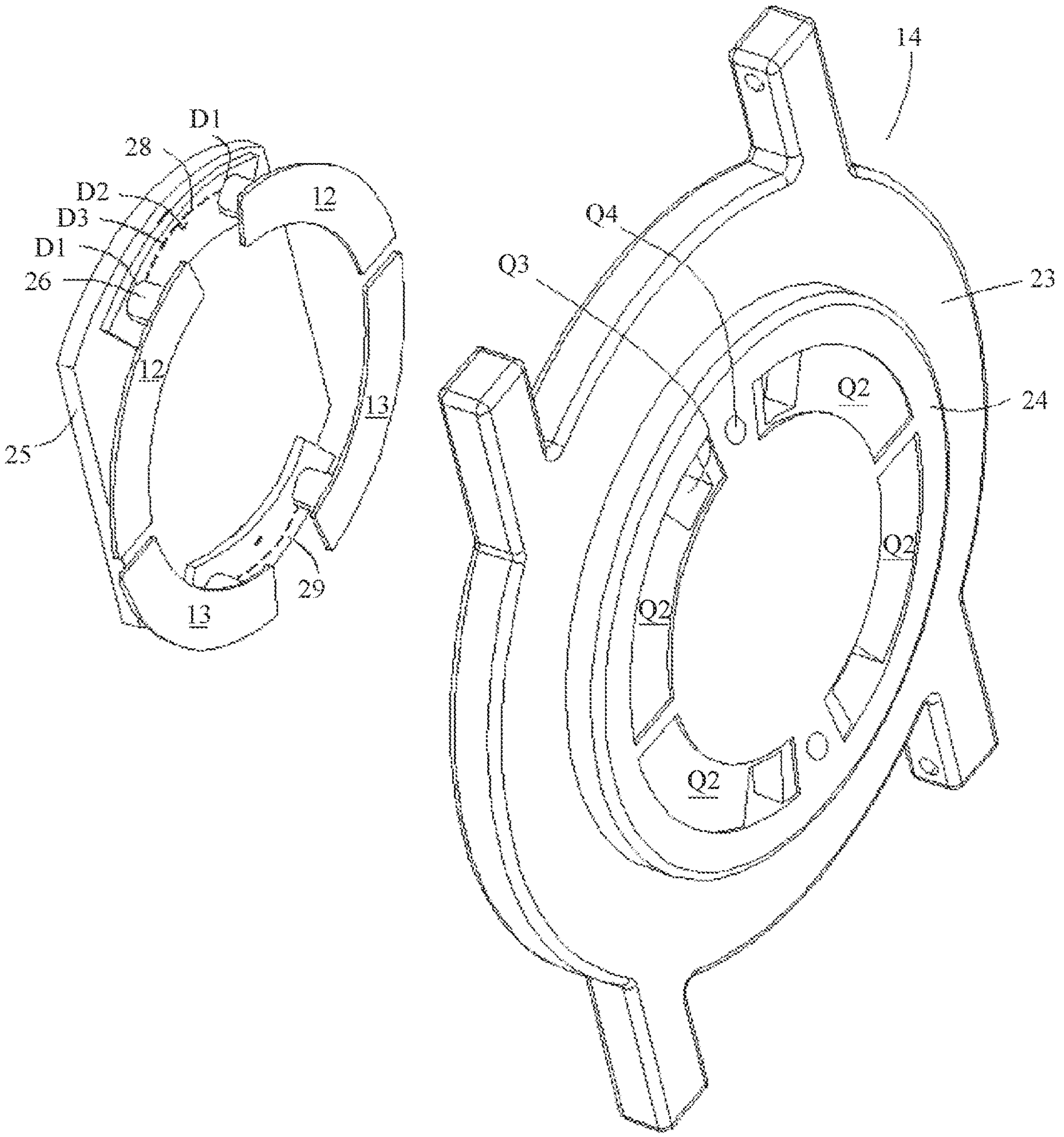
FIG. 7 is a three-dimensional expanded view of a partial structure of the electronic device in FIG. 4.

Referring to FIG. 5, in this implementation, the first contact area S1 and the second contact area S2 are distributed on the rear housing 14. The first contact area S1 and the second contact area S2 are two areas on the housing surface of the rear housing 14. The shape of the first contact area S1/the second contact area S2 is not specifically limited. For example, in the implementation shown in FIG. 5, the first contact area S1 and the second contact area S2 are respectively located on an upper side and a lower side of the housing surface of the rear housing 14. Referring to FIG. 5 to FIG. 7, the plurality of first contact electrodes 12 are spaced on the rear housing 14 and directly electrically connected on the inner side of the rear housing 14 or electrically connected to each other through an intermediate conductive structure. The first contact electrode 12 is at least partially exposed to an outer side of the rear housing 14. Similarly, the plurality of second contact electrodes 13 are spaced on the rear housing 14 and directly electrically connected on the inner side of the rear housing 14 or electrically connected to each other through an intermediate conductive structure. The second contact electrode 13 is at least partially exposed to the outer side of the rear housing 14. The first contact electrode 12/the second contact electrode 13 is exposed to the outer side of the housing 11 for contact with the skin of the wearer. Certainly, the exposure may be flush with an outer side surface of the rear housing 14, protrude from the outer side surface of the rear housing 14 or be concave from the outer side surface of the rear housing 14, as long as the skin 82 of the wearer 80 can be contacted without being blocked by other non-conductive structures. Preferably, the first contact electrode 12/the second contact electrode 13 is arranged to be flush with the outer side surface of the rear housing 14 or slightly protrude from the outer side surface of the rear housing 14, so as to improve the wear comfort based on reliable contact. The spacing between the plurality of first contact electrodes 12/the plurality of second contact electrodes 13 may be used for arranging other components, such as the charging pogo pin and a temperature sensor of the electronic device 10. For example, for some products such as the electronic watches 10*a*, it may be necessary to retain the original design of the charging pogo pin 17 to adapt to a universal charging base of the electronic watch 10*a*. These charging pogo pins 17 may need to penetrate the area where the electrode is located. In the conventional technology, a solution that the charging pogo pin 17 penetrates the contact electrode is adopted, causing a problem of interference between the charging pogo pin and the electrode or a complex waterproof structure at an intersection position. In this implementation, by arranging the plurality of first contact electrodes 12/second contact electrodes 13 spaced and electrically connected on the inner side of the rear housing 14, the charging pogo pin 17 may be arranged at the spacing. The structure arrangement on the rear housing 14 is proper, without affecting the arrangement of the charging pogo pin 17.

The first contact electrode 12 and the second contact electrode 13 in this embodiment of this application are used for contacting with the skin respectively to form the bioelectrical signal acquisition circuit. At least one first contact electrode 12 and at least one second contact electrode 13 are distributed in the first contact area S1, and at least one first contact electrode 12 and at least one second contact electrode 13 are distributed in the second contact area S2. Optionally, the first contact electrode 12 and the second contact electrode 13 are the ECG electrodes, used for acquiring a human electrocardiogram signal.

When the electronic device 10 in this implementation is worn, if the wear is normal or tight (referring to FIG. 2), the first contact area S1 and the second contact area S2 are both in contact with the skin of the wearer. In this case, because there are the plurality of first contact electrodes 12 and the plurality of second contact electrodes 13, it is easy to ensure that the first contact electrode 12 and the second contact electrode 13 are in contact with the skin. If the wear is loose (referring to FIG. 3), the housing 11 may tilt to one side due to gravity or other causes, so that one of the first contact area S1 and the second contact area S2 leaves the skin of the wearer. In this case, because the first contact electrode 12 and the second contact electrode 13 are both distributed in the first contact area S1, and the first contact electrode 12 and the second contact electrode 13 are also both distributed in the second contact area S2, even if the housing 11 tilts to one side, it can still be ensured that the first contact electrode 12 and the second contact electrode 13 are in contact with the skin.

In this implementation, the first contact area S1 and the second contact area S2 are spaced on the rear housing 14 along a first direction Y1 (the up-down direction shown in FIG. 5) and the rear housing 14 has a middle area S3 between the first contact area S1 and the second contact area S2. In this implementation, the middle area S3 may be used for separating the first contact area S1 and the second contact area S2, so that other structures of the electronic device 10, such as the charging pogo pin 17 (Pogo Pin) or other measuring electrodes/sensors, may be arranged between the two. The charging pogo pin 17 is arranged in the middle area S3, which can realize a charging function of the electronic device 10.

The shape of the rear housing 14 may be set as required, such as round, square, polygon or other shapes. For example, in the implementation shown in FIG. 1, the rear housing 14 is roughly square, and the four contact electrodes (including two first contact electrodes 12 and two second contact electrodes 13) on the rear housing 14 are distributed in a matrix. In another example, in the implementation shown in FIG. 5, the rear housing 14 is roughly circular, and the plurality of contact electrodes (including two first contact electrodes 12 and two second contact electrodes 13) on the rear housing 14 are circumferentially distributed. Certainly, the shape of the rear housing 14 does not need to correspond to the distribution mode of the contact electrode one by one. For example, for the square rear housing 14, the contact electrode thereon may also be arranged to be circumferentially distributed.

Figure 8:
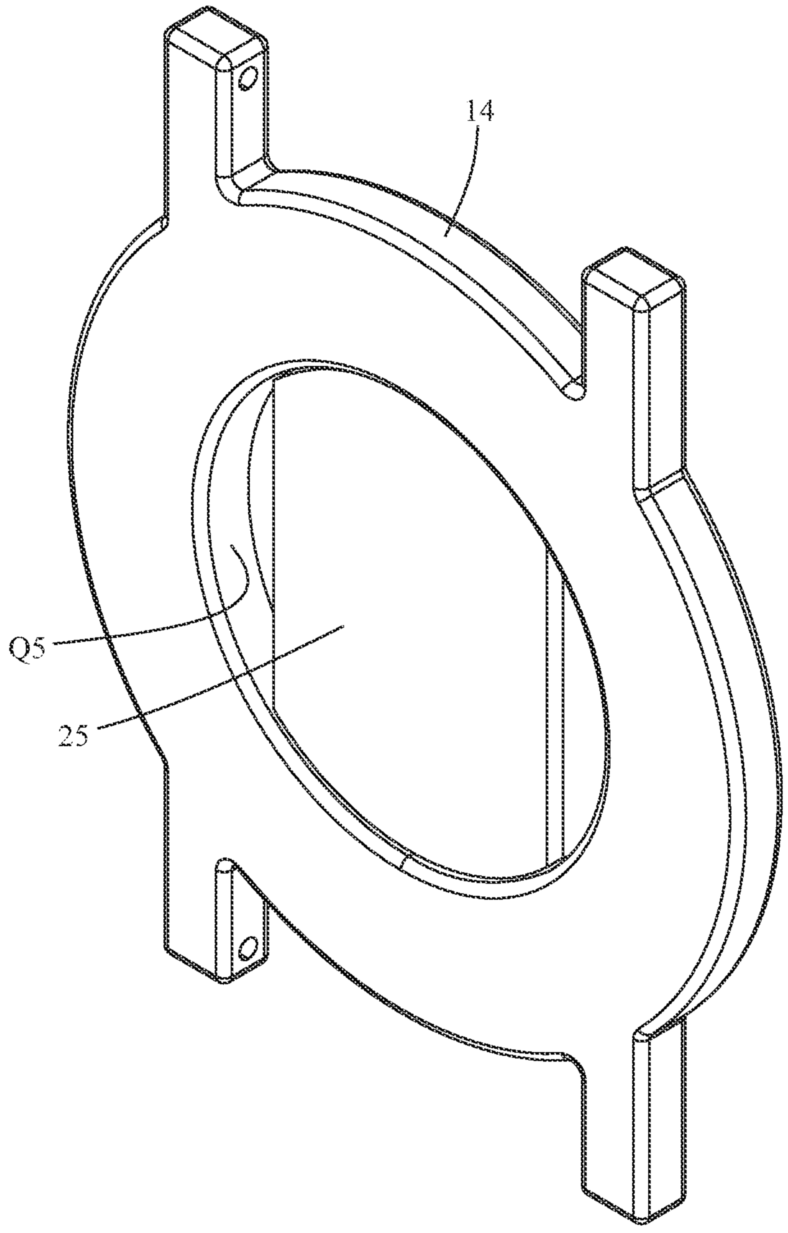
FIG. 8 is a three-dimensional view of a partial structure of the electronic device in FIG. 4 from another view.
Figure 9:
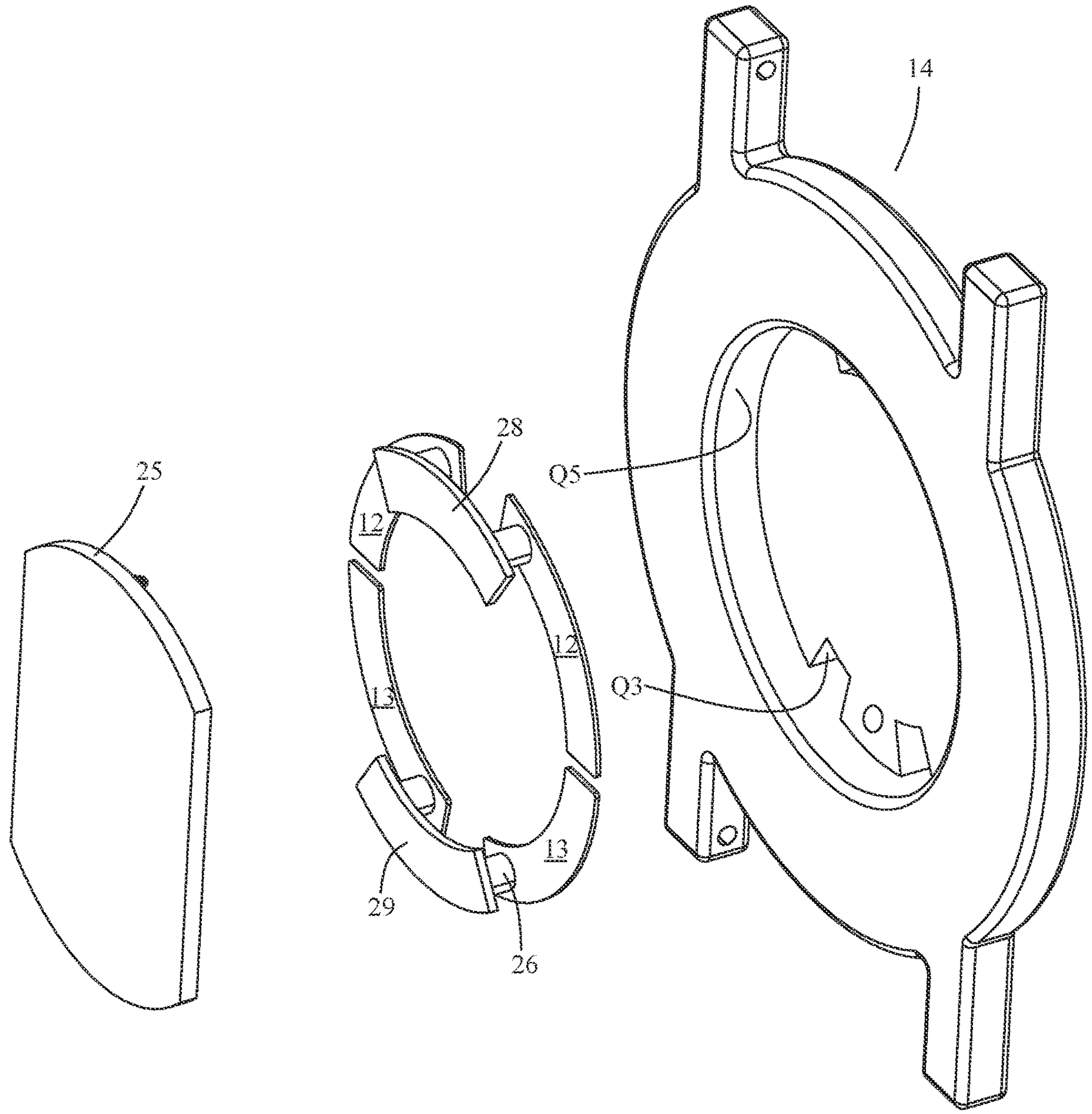
FIG. 9 is an expanded view of FIG. 8.
Figure 10:
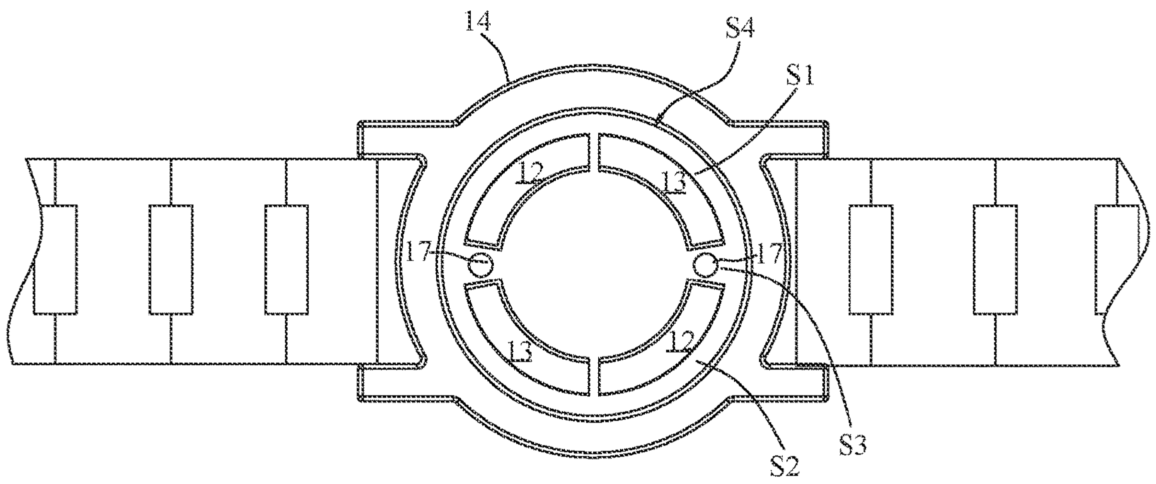
FIG. 10 is a schematic diagram of another implementation of the electronic device in FIG. 5.

Referring to FIG. 5, the rear housing 14 has an annular area S4 (referring to FIG. 7-FIG. 9) that is convex towards the rear, and a plurality of contact electrodes spaced apart from each other are distributed in the annular area S4 along the circumferential direction. One side (an upper part of the annular area S4 in FIG. 5) of the annular area S4 is the first contact area S1, and there is at least one first contact electrode 12 and one second contact electrode 13 among the contact electrodes distributed in the first contact area S1. Another side (a lower part of the annular area S4 in FIG. 5) of the annular area S4 is the second contact area S2, and there is at least one first contact electrode 12 and one second contact electrode 13 among the contact electrodes distributed in the second contact area S2. In this implementation, the convex annular area S4 arranged on the rear housing 14 is used for distributing and arranging the contact electrode, which is conducive to the contact between the contact electrode and the skin of the wearer. Optionally, a quantity of the contact electrodes is 2N, and N is a positive integer, where N contact electrodes are the first contact electrodes 12, and the other N contact electrodes are the second contact electrodes 13. The N first contact electrodes 12 are sequentially adjacent in the annular area S4 along the circumferential direction, and the N second contact electrodes 13 are sequentially adjacent in the annular area S4 along the circumferential direction. In other implementations, the N first contact electrodes 12 and the N second contact electrodes 13 may further be arranged alternately along the circumferential direction. Optionally, the contact electrode is arc-shaped. For example, as shown in FIG. 5, there are four contact electrodes in total, two first contact electrodes 12 and two second contact electrodes 13. The first contact electrodes 12 are sequentially adjacent, and the second contact electrodes 13 are sequentially adjacent, the first contact electrodes 12/the second contact electrodes 13 are distributed intensively, and the electrical connection wiring between the first contact electrodes 12/the second contact electrodes 13 is simple and convenient. In another example, as shown in FIG. 10, the first contact electrodes 12 and the second contact electrodes 13 are sequentially arranged alternately. That is, the two first contact electrodes 12 are arranged diagonally, and the two second contact electrodes 13 are arranged diagonally. In this arrangement mode, no matter whether the device body tilts to the left side, right side, upper side, or lower side (the left side, right side, upper side, and lower side are described according to the direction shown in FIG. 5, and are not limited), it can be ensured that at least one first contact electrode 12 and at least one second contact electrode 13 are in contact with the skin of the wearer to form the bioelectrical signal acquisition circuit. In the foregoing implementation, the contact electrode is arc-shaped, so that the contact electrodes can form a circular circumferential distribution form, which achieves beautiful appearance, and is conducive to the contact between the contact electrode and the skin of the wearer.

Figure 11:
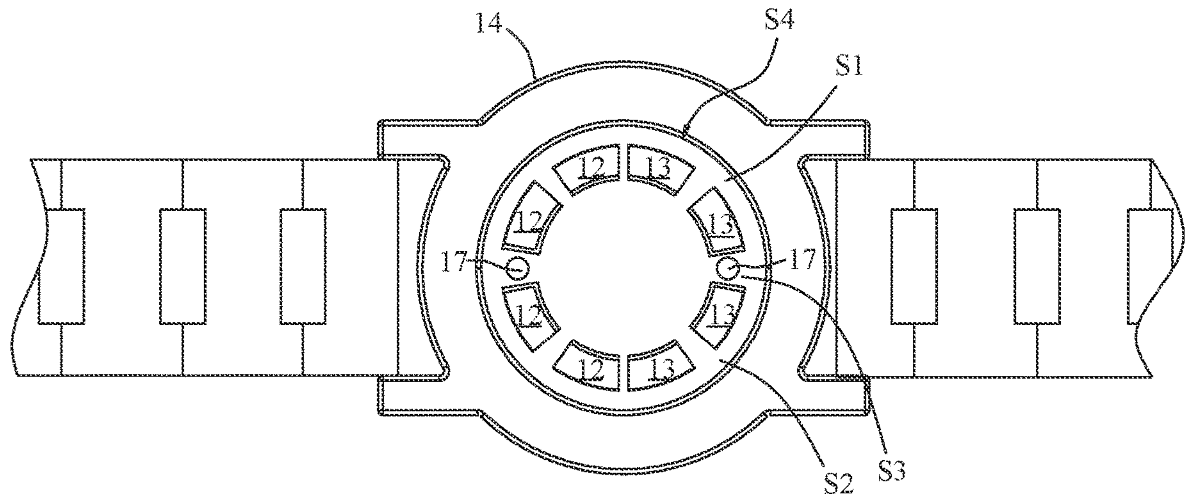
FIG. 11 is a schematic diagram of still another implementation of the electronic device in FIG. 5.

In the implementation as shown in FIG. 11, 8 contact electrodes are arranged, and the 8 contact electrodes are sequentially spaced along the circumferential direction. The four contact electrodes on the left side in FIG. 11 are the first contact electrodes 12, which are electrically connected on the inner side of the rear housing 14 (the electrical connection structure is not shown in FIG. 11). The four contact electrodes on the right side are the second contact electrodes 13 (the electrical connection structure is not shown in FIG. 11). In the rear housing 14, an upper area shown in the figure is the first contact area S1, a lower area is the second contact area S2, and the middle area S3 is between the first contact area S1 and the second contact area S2. The left side and right side of the middle area S3 are respectively arranged with the charging pogo pins 17 to match with the charging base (not shown in the figure) of the electronic device 10. In this way, when the electronic device 10 is worn, even if the upper side tilts or the lower side tilts, the other side can be ensured to contact with the skin of the wearer, so as to ensure that at least one first contact electrode 12 and one second contact electrode 13 are in contact with the skin of the wearer, thereby forming the bioelectrical signal acquisition circuit. In this implementation, 8 contact electrodes are arranged on the rear housing 14, and there are more spacings between the adjacent contact electrodes on the rear housing 14, so that more detection elements, such as a force sensor and an optical sensor, may be arranged on the rear housing 14, to increase data that can be detected by the electronic device 10.

It should be noted that the quantity of the first contact electrodes 12 may be equal or not equal to the quantity of the second contact electrodes 13. The quantity of the first contact electrodes 12/the second contact electrodes 13 may be an odd number or an even number.

Referring mainly to FIG. 5 and FIG. 7, in a possible implementation, the rear housing 14 includes a main housing plate 23 and a circular plate 24 protruding outwards from a central position of the main housing plate 23. The first contact area S1 and the second contact area S2 are both located on the circular plate 24. This implementation is favorable for the first contact area S1 and the second contact area S2 to contact with the skin of the wearer. Optionally, a plurality of accommodating slots Q2 spaced along the circumferential direction are provided on an outer side surface of the circular plate 24, and the accommodating slots Q2 are used for accommodating the first contact electrodes 12 or the second contact electrodes 13. The accommodating slot Q2 does not penetrate the circular plate 24, and the depth may be slightly less than the thickness of the corresponding first contact electrode 12/second contact electrode 13. The first contact electrode 12 and the second contact electrode 13 are respectively exposed to the outer side surface of the circular plate 24. This implementation is conducive to the determining of the positions of the first contact electrode 12 and the second contact electrode 13, and during wear, the first contact electrode 12 and the second contact electrode 13 can be pressed between the skin of the wearer and a bottom surface of the accommodating slot Q2, which is favorable for the first contact electrode 12 and the second contact electrode 13 to contact with the skin of the wearer.

Figure 13:
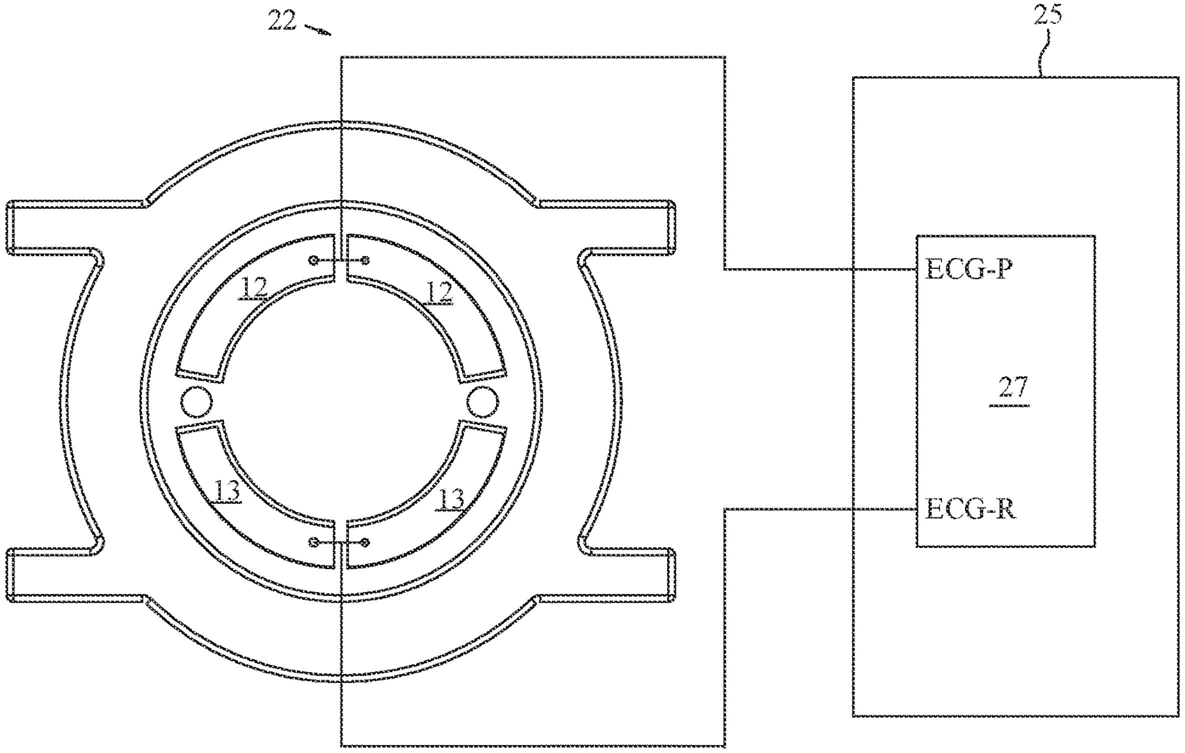
FIG. 13 is a schematic diagram of a bioelectrical signal acquisition circuit of the electronic device in FIG. 5.

Referring to FIG. 5-FIG. 9, in this implementation, the dial 18 further includes a printed circuit board 25. Optionally, when the circular plate 24 of the rear housing 14 is convex, a groove Q5 is formed on the inner side of the housing, and the matching printed circuit board 25 may be installed in the groove Q5. The groove Q5 may be part of the foregoing internal space Q1. The first contact electrode 12 and/or the second contact electrode 13 are electrically connected to the printed circuit board 25 through a conductive member 26. The conductive member 26 may be conductive foam or a conductive metal dome. The first contact electrode 12 and/or the second contact electrode 13 receive a bioelectrical signal from the skin of the wearer and can transmit the bioelectrical signal to the printed circuit board 25 through the conductive foam or the conductive metal dome for processing and analysis. The conductive foam or the conductive metal dome has a certain elasticity, and can adapt to the jumping of the spacing between the first contact electrode 12/the second contact electrode 13 and the printed circuit board 25 within a certain range, which is conducive to the reliability of electrical connection. Optionally, referring to FIG. 13, the printed circuit board 25 includes an AFE chip 27. The AFE chip 27 is electrically connected to the first contact electrode 12 and the second contact electrode 13 respectively to acquire and/or process electrical signals from the first contact electrode 12 and the second contact electrode 13. The AFE chip 27 can pre-sample the signals transmitted by the first contact electrode 12 and the second contact electrode 13. In an implementation, the first contact electrode 12/the second contact electrode 13 is an ECG electrode. The corresponding AFE chip 27 has an ECG-P interface for being electrically connected to the first contact electrode 12 and an ECG-R interface for being electrically connected to the second contact electrode 13. The first contact electrode 12 is electrically connected to the ECG-P interface, and the second contact electrode 13 is electrically connected to the ECG-R interface to form a bioelectrical signal acquisition circuit 22. In this way, the signals acquired by the first contact electrode 12/the second contact electrode 13 are respectively transmitted to the AFE chip 27. The AFE chip 27 initially acquires and processes the signals and then transmits the signals to a main processing chip of the printed circuit board for processing.

Referring mainly to FIG. 7, in this implementation, through holes Q3 penetrating from the bottom surfaces of the accommodating slots Q2 to an inner side surface of the circular plate 24 are provided on the circular plate 24. A first conductive plate 28 and a second conductive plate 29 are arranged on the inner side of the rear housing 14. The first contact electrodes 12 are electrically connected to the first conductive plate 28 through a conductive member 26 penetrating the corresponding through holes Q3, and the second contact electrodes 13 are electrically connected to the second conductive plate 29 through a conductive member 26 penetrating the corresponding through holes Q3. The conductive member 26 may be conductive foam or a conductive metal dome, and the area thereof may be set above 5 $mm^2$. In this implementation, the conductive connection of the first contact electrodes 12 and the conductive connection of the second contact electrodes 13 are respectively implemented through the first conductive plate 28 and the second conductive plate 29 arranged on the inner side of the rear housing 14. Optionally, the accommodating slot Q2 is arc-shaped and suitable for matching with the arc-shaped contact electrode. Optionally, the first conductive plate 28 and the second conductive plate 29 are also arc-shaped. The first conductive plate 28 and the second conductive plate 29 may adopt a flexible printed circuit. The first conductive plate 28 and the second conductive plate 29 may be accommodated in the groove Q5 and located between the printed circuit board 25 and the circular plate 24.

The electronic device 10 in this implementation further includes two charging pogo pins 17 (shown in FIG. 5), where one charging pogo pin 17 is located between two adjacent first contact electrodes 12, and the other charging pogo pin 17 is located between two adjacent second contact electrodes 13. The two charging pogo pins 17, the first contact electrode 12, and the second contact electrode 13 are basically distributed in an annular area. This arrangement mode is compatible with the previous generation charging base with the charging contact points matching the charging pogo pins 17 arranged at the corresponding positions, and has the effects of good contact reliability with skin 82 and better adaptation to different wear states, as described above.

In this implementation, two vias Q4 are further provided on the circular plate 24, and the via is used for allowing the charging pogo pin 17 to be exposed to the outer side surface of the circular plate 24. The via Q4 is located on the circumference where the accommodating slots Q2 are located and at a position of the circular plate 24 between the adjacent accommodating slots Q2. In this implementation, the charging pogo pin 17 and the contact electrodes are both arranged on the circular plate 24, so that the space arrangement is proper. While the problems of complex structural coordination and poor sealing caused by the charging pogo pin 17 penetrating the contact electrode are avoided, the proper distribution of the first contact electrode 12 and the second contact electrode 13 is ensured, so as to facilitate the formation of the bioelectrical signal acquisition circuit 22.

Referring mainly to FIG. 7, the first conductive plate 28/the second conductive plate 29 adopts an arc-shaped printed circuit board. First contact points D1 are respectively arranged near two ends of the arc direction. A conductive circuit D3 that electrically connects the two first contact points is arranged inside. A second contact point D2 is arranged in the middle of the arc direction of the first conductive plate 28/the second conductive plate 29. There is no electric conduction between the second contact point D2 and the first contact point D1 or the conductive circuit D3.

The two first contact points D1 of the first conductive plate 28/the second conductive plate 29 are respectively used for electrically connecting the two conductive members 26 corresponding to the first contact electrode 12/the second contact electrode 13, to access two first contact electrodes 12/the second contact electrodes 13, and further access the ECG-P interface/the ECG-R interface of the AFE chip 27 to form the bioelectrical signal acquisition circuit 22.

The two charging pogo pins 17 penetrate the corresponding vias Q4 and then are electrically connected to the second contact point D2 of the first conductive plate 28/the second conductive plate 29, and may access a charging circuit of the electronic device 10. Certainly, in other implementations, the first conductive plate 28/the second conductive plate 29 may not be arranged with the second contact point D2, but a through cutting groove (not shown in the figure) is provided on the first conductive plate 28/the second conductive plate 29. The charging pogo pin 17 penetrates the first conductive plate 28/the second conductive plate 29 from the cutting groove and then is directly conductively welded and fixed at the corresponding position of the printed circuit board 25.

Figure 12:
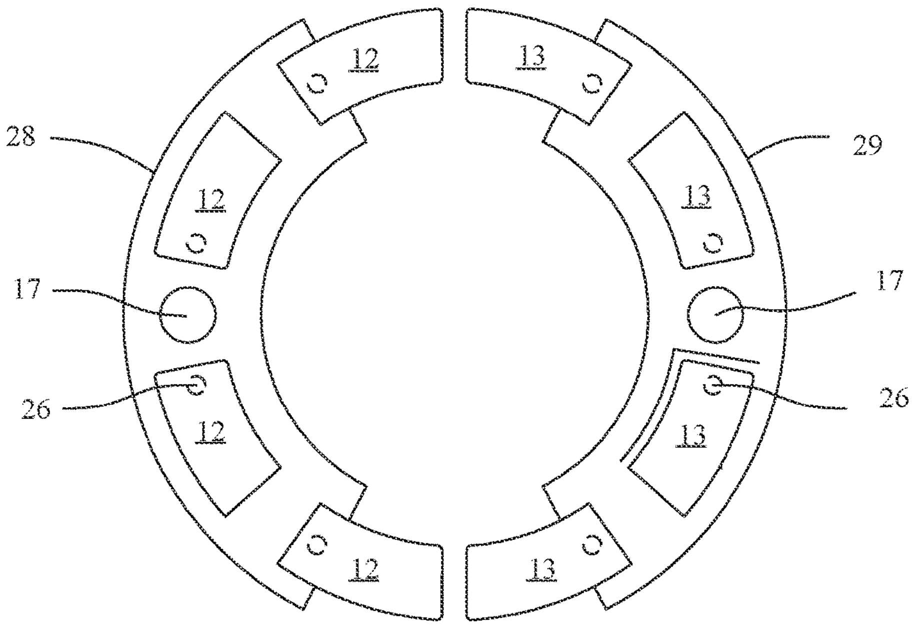
FIG. 12 is a connection diagram of contact electrodes and a first conductive plate/a second conductive plate of the electronic device in FIG. 11.

In this arrangement mode, by arranging the contact points of the first conductive plate 28/the second conductive plate 29 and the conductive circuit D3, the first contact electrodes 12, the second contact electrodes 13, and the charging pogo pins 17 can properly access the corresponding circuit inside the electronic device 10, and the structure is simple and proper. Referring to FIG. 12, for the implementation in which there are four first contact electrodes 12/second contact electrodes 13 respectively as shown in FIG. 11, an extension range of the arc direction of the first conductive plate 28/the second conductive plate 29 may be made to cover the conductive members 26 of the first contact electrodes 12/the second contact electrodes 13 and the corresponding charging pogo pins 17 based on the arrangement mode in FIG. 7. In this way, all the first contact electrodes 12/second contact electrodes 13 and the corresponding charging pogo pins 17 can be conveniently and electrically connected to the first conductive plate 28/the second conductive plate 29 correspondingly. For example, the conductive connection between the first contact electrode 12/the second contact electrode 13 and the charging pogo pin 17 and the first conductive plate 28/the second conductive plate 29 is implemented by adopting the method that the contact points and the conductive circuit are arranged on the first conductive plate 28/the second conductive plate 29.

Figure 14:
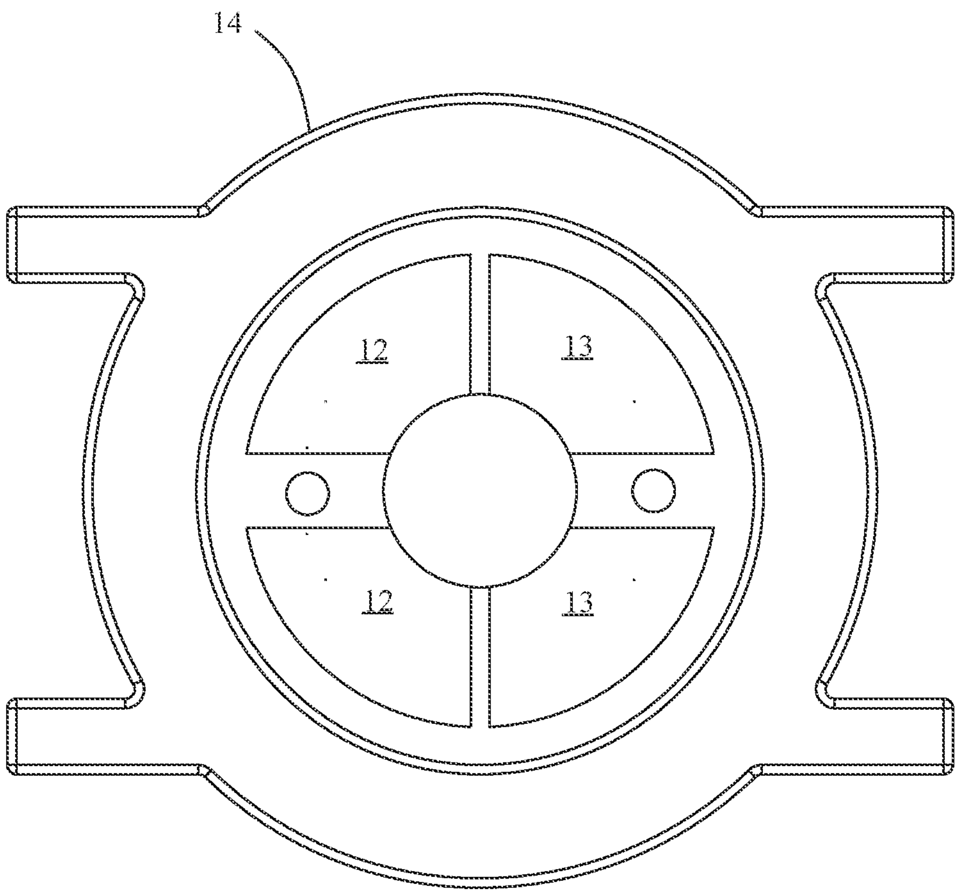
FIG. 14 is a partial structural view of an electronic device with another electrode structure form.
Figure 15:
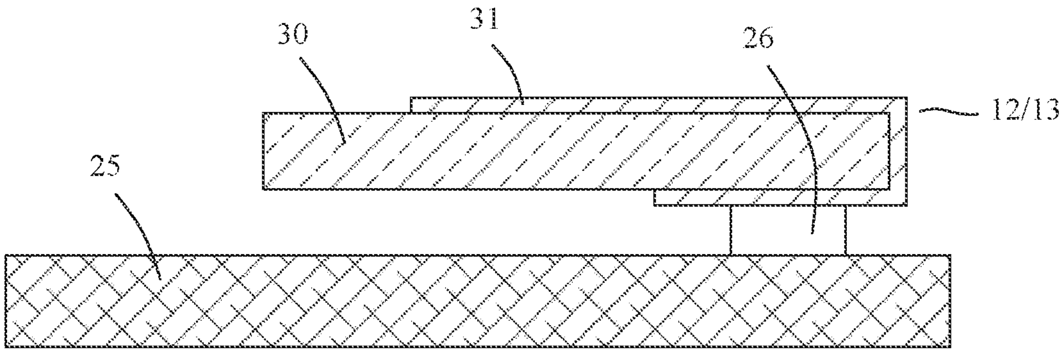
FIG. 15 is a schematic structural diagram of electrical connection of a first contact electrode/second contact electrode and a printed circuit board in the implementation in FIG. 14.

In other embodiments, referring to FIG. 14 and FIG. 15, the first contact electrode 12 and/or the second contact electrode 13 may further be arranged to include a substrate 30 and a conductive layer 31 on a surface of the substrate 30. In this implementation, contact conduction is implemented through the conductive layer 31 arranged on the surface of the substrate 30. The substrate 30 may be made of non-conductive materials such as glass. The conductive layer 31 may be formed by coating, electroplating, chemical deposition or other methods, and may be metal conductive materials such as chromium or zirconium. For example, a chromium layer/a zirconium layer is formed by plating on the glass substrate 30 to form the first contact electrode 12 and/or the second contact electrode 13. The first contact electrode 12 and/or the second contact electrode 13 in this form may be electrically connected to the printed circuit board 25 with the conductive layer 31 through the conductive member 26. Certainly, as described above, in some implementations, the conductive member 26 may be conductive foam or a conductive metal dome. The shape of the first contact electrode 12 and/or the second contact electrode 13 in this form may be the same or different from that in the foregoing implementations.

Referring to FIG. 4 and FIG. 5 again, as described above, the electronic device 10 in this implementation is the electronic watch 10*a*. The rear housing 14 has a first connecting ear 32 and a second connecting ear 33 oppositely arranged along a second direction Y2 (the left-right direction shown in FIG. 5), and two ends of the chain 19 are respectively connected to the first connecting ear 32 and the second connecting ear 33 to form a circle with the dial 18 for being worn on a human wrist 81. The first contact area S1 and the second contact area S2 are spaced on the rear housing 14 along a first direction Y1 (the up-down direction shown in FIG. 5) and the rear housing 14 has a middle area S3 between the first contact area S1 and the second contact area S2. The electronic watch 10*a* further includes two charging pogo pins 17, and the two charging pogo pins 17 are spaced in the middle area S3 along the second direction Y2. When the electronic watch 10*a* is worn on the human wrist 81, the first direction Y1 is a long direction along the human wrist, and the second direction Y2 is a long direction perpendicular to the human wrist. The electronic device 10 in this implementation is the electronic watch 10*a*, and a natural state of hands of the wearer is that the hands hang down (referring to FIG. 2 or FIG. 3). In this case, the first direction Y1 is along a gravity direction. That is, the first contact area S1 and the second contact area S2 are distributed up and down. When the wear is tight, it can be ensured that the first contact area S1 and the second contact area are S2 both in contact with the wrist to ensure the acquisition of the bioelectrical signal. When the wear is loose, the dial 18 of the electronic watch 10*a* is restrained by gravity and the chain 19. Although the upper one of the first contact area S1 and the second contact area S2 tilts and leaves the wrist skin, the lower one of the first contact area S1 and the second contact area S2 is pressed against the wrist skin. That is, one of the first contact area S1 and the second contact area S2 is in contact with the wrist skin. In addition, either of the first contact area S1 and the second contact area S2 is arranged with the first contact electrode 12 and the second contact electrode 13, so that the bioelectrical signal can also be acquired.

In conclusion, the electronic device 10 in this embodiment of this application has the beneficial effects of good contact reliability with the skin of the wearer, reliable acquisition of the bioelectrical signal, and taking into account the arrangement of some electrodes when the position of the charging pogo pin 17 cannot be moved.

An embodiment of this application further provides a bioelectrical signal acquisition method. A detected object wears the foregoing electronic device 10, and at least one of the first contact area S1 or the second contact area S2 is made to contact with skin 82 of the detected object, so that at least one first contact electrode 12 and at least one second contact electrode 13 are in contact with the skin 82 of the detected object to form a bioelectrical signal acquisition circuit 22, thereby acquiring a bioelectrical signal of the detected object. Optionally, the bioelectrical signal is an electrocardiogram signal or a body composition electrical signal. The bioelectrical signal acquisition method in this embodiment of this application adopts the foregoing electronic device 10, which can adapt to the requirements of acquiring the bioelectrical signal when the wear is loose or tight, and ensure the reliability of signal acquisition.

The foregoing implementations are merely intended for describing the technical solutions of this application but not for limiting this application. Although this application is described in detail with reference to the exemplary implementations, a person of ordinary skill in the art should understand that modifications or equivalent replacements may be made to the technical solutions of this application without departing from the spirit and scope of this application.

What is claimed is:

1. An electronic device, comprising:

a housing comprising a rear housing, wherein a first contact area and a second contact area are distributed on the rear housing;

a first set of contact electrodes, wherein contact electrodes in the first set of contact electrodes are spaced on the rear housing and electrically connected to each other on an inner side of the rear housing, and wherein a first contact electrode and a second contact electrode of the first set of contact electrodes are at least partially exposed to an outer side of the rear housing; and a second set of contact electrodes, wherein contact electrodes in the second set of contact electrodes are spaced on the rear housing and electrically connected to each other on the inner side of the rear housing, wherein a third contact electrode and a fourth contact electrode of the second set of contact electrodes are at least partially exposed to the outer side of the rear housing, and wherein the first and second contact electrodes of the first set of contact electrodes are insulated from the third and fourth contact electrodes of the second set of contact electrodes;

wherein at least one contact electrode from the first set of contact electrodes and at least one contact electrode from the second set of contact electrodes are distributed in the first contact area, and at least one contact electrode from the first set of contact electrodes and at least one contact electrode from the second set of contact electrodes are distributed in the second contact area;

wherein the rear housing has a convex annular area;

wherein an upper annular area of the convex annular area is the first contact area and includes a first portion of a first conductive plate and a first portion of a second conductive plate, wherein the first conductive plate is electrically connected to the first contact electrode from the first set of contact electrodes and the second conductive plate is electrically connected to the third contact electrode from the second set of contact electrodes distributed in the upper annular area;

wherein a lower annular area of the convex annular area is the second contact area and includes a second portion of the first conductive plate and a second portion of the second conductive plate, wherein the first conductive plate is electrically connected to the second contact electrode from the first set of contact electrodes and the second conductive plate is electrically connected to the fourth contact electrode from the second set of contact electrodes distributed in the lower annular area;

wherein the first conductive plate is electrically connected to the first and second contact electrodes from the first set of contact electrodes through first conductive members penetrating a first set of holes in the housing; and wherein the second conductive plate is electrically connected to the third and fourth contact electrodes from the second set of contact electrodes through second conductive members penetrating a second set of holes in the housing.

2. The electronic device according to claim 1, wherein the first contact area and the second contact area are spaced on the rear housing along a first direction, and the rear housing has a middle area between the first contact area and the second contact area.

3. The electronic device according to claim 2, further comprising:

a charging pogo pin, wherein the charging pogo pin is arranged in the middle area.

4. The electronic device according to claim 1, wherein a plurality of contact electrodes spaced from each other are distributed in the convex annular area along a circumferential direction.

5. The electronic device according to claim 4, wherein a quantity of the plurality of contact electrodes is 2N, and N is a positive integer, wherein N contact electrodes are comprised in the first set of contact electrodes, and the other N contact electrodes are comprised in the second set of contact electrodes; and wherein:

the N contact electrodes in the first set of contact electrodes are sequentially adjacent in the convex annular area along the circumferential direction, and the N contact electrodes in the second set of contact electrodes are sequentially adjacent in the convex annular area along the circumferential direction; or the N contact electrodes in the first set of contact electrodes and the N contact electrodes in the second set of contact electrodes are arranged alternately along the circumferential direction.

6. The electronic device according to claim 1, wherein the rear housing comprises a main housing plate and a circular plate protruding outwards from a central position of the main housing plate; and wherein the first contact area and the second contact area are both located on the circular plate.

7. The electronic device according to claim 6, wherein a plurality of accommodating slots spaced along the circumferential direction are provided on an outer side surface of the circular plate, and the plurality of accommodating slots are used for accommodating the first set of contact electrodes or the second set of contact electrodes; and wherein the first set of contact electrodes and the second set of contact electrodes are respectively exposed to the outer side surface of the circular plate.

8. The electronic device according to claim 7, wherein through holes penetrating from bottom surfaces of the accommodating slots to an inner side surface of the circular plate are further provided on the circular plate; and wherein the first conductive plate and the second conductive plate are arranged on the inner side of the rear housing.

9. The electronic device according to claim 8, further comprising:

a charging pogo pin;

wherein a via is further provided on the circular plate, and the via is used for allowing the charging pogo pin to be exposed to the outer side surface of the circular plate; and wherein the via is located on the circumference where the accommodating slots are located and at a position of the circular plate between the adjacent accommodating slots.

10. The electronic device according to claim 6, wherein the housing comprises a main frame, the main frame has a front opening and a rear opening, and the rear housing is connected to the rear opening of the main frame.

11. The electronic device according to claim 1, wherein:

at least one of the first contact electrode or the third contact electrode are made of conductive materials; or at least one of the first contact electrode or the third contact electrode comprise a substrate and a conductive layer on a surface of the substrate.

12. The electronic device according to claim 1, wherein the housing further comprises a printed circuit board; and wherein at least one of the first contact electrode or the third contact electrode are electrically connected to the printed circuit board through a third conductive member.

13. The electronic device according to claim 12, wherein the third conductive member is conductive foam or a conductive metal dome.

14. The electronic device according to claim 12, wherein the printed circuit board comprises an analog front-end (AFE) chip, and the AFE chip is electrically connected to the first contact electrode and the third contact electrode respectively to acquire and/or process electrical signals from the first contact electrode and the third contact electrode.

15. The electronic device according to claim 1, wherein the electronic device is an electronic watch or an electronic bracelet.

16. The electronic device according to claim 1, wherein the electronic device is an electronic watch, and the housing is a dial of the electronic watch;

wherein the electronic watch comprises a chain connected to the housing, the housing has a first connecting ear and a second connecting ear oppositely arranged along a second direction, and two ends of the chain are respectively connected to the first connecting ear and the second connecting ear to form a loop with the housing for being worn on a human wrist;

wherein the first contact area and the second contact area are spaced on the rear housing along a first direction, and the rear housing has a middle area between the first contact area and the second contact area;

wherein the electronic watch further comprises two charging pogo pins, and the two charging pogo pins are spaced in the middle area along the second direction; and wherein when the electronic watch is worn on the human wrist, the first direction is a long direction along the human wrist, and the second direction is a long direction perpendicular to the human wrist.

17. The electronic device according to claim 1, wherein the first contact electrode and the third contact electrode are electrocardiogram (ECG) electrodes or body composition detection electrodes.

18. A bioelectrical signal acquisition method, comprising:

wearing, by a detected object, an electronic device, wherein the electronic device comprises:

a housing comprising a rear housing, wherein a first contact area and a second contact area are distributed on the rear housing;

a first set of contact electrodes, wherein contact electrodes in the first set of contact electrodes are spaced on the rear housing and electrically connected to each other on an inner side of the rear housing, and wherein a first contact electrode and a second contact electrode of the first set of contact electrodes are at least partially exposed to an outer side of the rear housing; and a second set of contact electrodes, wherein contact electrodes in the second set of contact electrodes are spaced on the rear housing and electrically connected to each other on the inner side of the rear housing, wherein a third contact electrode and a fourth contact electrode of the second set of contact electrodes are at least partially exposed to the outer side of the rear housing, and wherein the first and second contact electrodes of the first set of contact electrodes are insulated from the third and fourth contact electrodes of the second set of contact electrodes;

wherein at least one contact electrode from the first set of contact electrodes and at least one contact electrode from the second set of contact electrodes are distributed in the first contact area, and at least one contact electrode from the first set of contact electrodes and at least one contact electrode from the second set of contact electrodes are distributed in the second contact area;

wherein the rear housing has a convex annular area;

wherein an upper annular area of the convex annular area is the first contact area and includes a first portion of a first conductive plate and a first portion of a second conductive plate, wherein the first conductive plate is electrically connected to the first contact electrode from the first set of contact electrodes and the second conductive plate is electrically connected to the third contact electrode from the second set of contact electrodes distributed in the upper annular area;

wherein a lower annular area of the convex annular area is the second contact area and includes a second portion of the first conductive plate and a second portion of the second conductive plate, wherein the first conductive plate is electrically connected to the second contact electrode from the first set of contact electrodes and the second conductive plate is electrically connected to the fourth contact electrode from the second set of contact electrodes distributed in the lower annular area;

wherein the first conductive plate is electrically connected to the first and second contact electrodes from the first set of contact electrodes through first conductive members penetrating a first set of holes in the housing; and wherein the second conductive plate is electrically connected to the third and fourth contact electrodes from the second set of contact electrodes through second conductive members penetrating a second set of holes in the housing.

19. The bioelectrical signal acquisition method according to claim 18, wherein the bioelectrical signal is an electrocardiogram (ECG) signal or a body composition electrical signal.

* * * * *